United States Patent [19]
Kuo et al.

[11] Patent Number: 5,652,362
[45] Date of Patent: Jul. 29, 1997

[54] PREPARATION OF CAPROLACTAM

[75] Inventors: Pine-Sci Kuo, Chupei; Shiao-Jung Chu, Hsinchu; Chu-Ching Dai, Hsinchu Hsien; Ching-Tang Lin, Hsinchu; Hsi-Yen Hsu, Taipei, all of Taiwan

[73] Assignees: Industrial Technology Research Institute, Hsinchu; Acelon Chemicals and Fibers Corporation, Chang-Hua, both of Taiwan

[21] Appl. No.: 643,819

[22] Filed: May 6, 1996

[51] Int. Cl.$^6$ .................................................. C07D 201/08
[52] U.S. Cl. .................................................. 540/538
[58] Field of Search .................................................. 540/538

[56] References Cited

U.S. PATENT DOCUMENTS 5,502,185  3/1996  Fuchs et al. ........................... 540/538

*Primary Examiner*—Robert T. Bond
*Attorney, Agent, or Firm*—W. Wayne Liauh

[57] ABSTRACT

A method of making caprolactam from aminohexanoic acid or aminohexanoate ester comprising the steps of: (a) obtaining a reactor containing at least one catalyst, the catalyst being a metal oxide having acid-base-paired active sites; (b) charging a reaction feed into the reactor, the reaction feed containing a reactant, which is either amniohexanoic acid or $C_1$ to $C_{12}$ alkyl aminohexanoate ester, and a solvent; (c) reacting the reaction feed at a reaction temperature between 140° and 300° C. and a reaction pressure between 10 and 100 atm, to form a product stream; and (d) separating caprolactam from the product stream. The metal oxide catalyst is prepared from a process comprising the steps of: (a) dissolving at least a metal salt, which is not a metal oxide, in a solvent to form a metal salt solution, wherein: (i) the metal salt contains a metal element selected from the group consisting of silicon, titanium, tin, barium, calcium, magnesium, aluminum, and zinc; (ii) the solvent is selected from the group consisting of water, alcohol, ether, and mixtures thereof, and (iii) the metal salt is a salt which is soluble in the solvent; (b) adjusting the pH of the metal salt solution to be between 8 and 11, to thereby cause a precipitation of metal hydroxide; and (c) calcining the metal hydroxide at 300° to 1,000° C. to form a metal oxide.

12 Claims, No Drawings

PREPARATION OF CAPROLACTAM

FIELD OF THE INVENTION

The present invention relates to an improved method for making caprolactam, which can be subsequently used as a raw material for making Nylon 6. More specifically, the present invention relates to an improved method for making caprolactam from aminohexanoic acid or aminohexanoate. The method disclosed in the present invention exhibits many superior advantages, including high reaction rate at relatively low reaction temperature, extremely high reactant conversion and reaction yield, flexibility to use relatively inexpensive solvents during reaction, and minimum waste disposal problems. Another superior advantage of the method disclosed in the present invention is that it allows high reactant concentrations to be employed in the reaction, at least about twice as high as those allowed in the prior art processes, so as to enable increased caprolactam production. Because of these advantageous features provided by the method disclosed in the present invention, the cost of making caprolactam is substantially reduced.

BACKGROUND OF THE INVENTION

Caprolactam (i.e., 2-oxohexamethylenimine, hexahydro-2H-azepin-2-one) is one of the most widely used chemical intermediates; it a very important raw material for making man-made fibers, more specifically Nylon 6 polymers. Its annual consumption is in the range of millions of tons. Nylon 6 has been commercially used in a very wide variety of applications, such as: in the fiber industry for making Nylon fibers, cotton-like Nylon fibers; the fabric made from Nylon 6 can be used in making garments, panty hose, umbrella canopies, window curtains, carpets, etc; in fishing industry for making fishing nets, fishing lines, ropes, etc; in manufacturing industry for making tires, conveyer belts, transmission belts; for use as an engineering plastics for making gears, beatings, industrial parts, etc. Additionally, caprolactam itself can be used in many applications, such as making paints, plasticizers, synthetic leathers, lacquer, etc.

Conventionally the production of caprolactam uses benzene as the raw material, by which benzene is hydrogenated to form cyclohexane, which is then oxidized to become cyclohexanol and cyclohexanone. Subsequent reaction with ammonia-derived hydroxylamine forms cyclohexanone oxime which undergoes a Beckmann molecular rearrangement to from the seven-membered ring caprolactam, or more specifically, ε-caprolactam. The conventional process suffers several shortcomings, including relatively complicated manufacturing procedure and low reaction yield (only about 5 mole %). The conventional process also suffers from the problem of large reaction waste Typically, every kilogram of caprolactam production would generate about 2.8 kilograms of ammonium sulfate, a reaction by-product. These shortcomings cause the high cost of caprolactam to be maintained at an undesirably high level.

Alternative routes of producing caprolactam utilizing aminohexanoate (esters of aminohexanoic acids) have recently generated interests. German Pat. DE-2,249,993 discloses a process in which 6-aminohexanoate is heated, in a water-containing environment, at 250°~350° C. to form caprolactam. The main disadvantage of this process is that the concentration of the raw material must be very low, so as prevent oligmers from being formed. The low caprolactam concentration in the reaction product, as a result of the low reactant concentration, causes the post-production separation very difficult and expensive.

German Pat. DE-3,235,938 discloses a process by which polyols with a boiling point greater than caprolactam, such as tetraethylene glycol, diglycerol, butanetriol, etc., are used as reaction solvent. With this process, thermal stability of the reactants can be a problem and large amounts of reaction by-products are produced, resulting in very poor selective yield of caprolactam. In Japanese Pat. 14,563, it is disclosed a process which uses ethanediol as reaction solvent at a reaction temperature of 160°~165° C. for 4 hours. However, the results show that, not only the reaction yield of caprolactam was very low, it was very difficult to separate the reaction product caprolactam from the reaction solvent ethanediol. In U.S. Pat. No. 4,767,856, (the '856 patent) it is disclosed a process by which a heavy oil with a boiling point between 350°~550° C., such as white oil, vacuum oil, molten wax, etc., was used as reaction solvent. Results from '856 process showed good conversion from methyl aminohexanoate and good selectivity of caprolactam. However, the reaction must be conducted at temperatures of 250°~330° C., and the raw material concentration was limited to 3~7.5 wt %. These are the some of disadvantages of the '856 process.

German Patent DE-3,843,793 and U.S. Pat. No. 4,963,673 discloses a process in which aromatics having a boiling point between 110°~200° C., such as toluene, xylene, etc, were used as the reaction medium, with a small amount of water added to increase the solubility of the raw material. This reaction medium ameliorates the separation problem that exists between caprolactam and solvent discussed above. Two types of reactors were disclosed: a continuous fixed bed type reactor and a batch type high pressure reactor. Reaction results indicated that with a fixed bed reactor, when the concentration of methyl aminohexanoate exceeded 9.3 wt %, the yield of caprolactam would decrease to below 65 mol %. Additionally, the use of toluene or xylene often caused phase separation problems in the intermediate reaction products, and substantial amounts of water must be added while, at the same time, the concentrations of toluene or xylene must be increased to at least 80 wt % in order to increase the solubility of the raw material (i.e., reactants). This would result in the expenditure of large amounts of effort for subsequent solvent recovery and causing problems during mass productions. On the other hand, with a batch type reactor, the reaction yields of caprolactam were all less than 80 mol %.

German Patent DE-3,823,213 discloses a process by which the reaction yield of caprolactam can be increased to 82 mol %. However, this process requires a reaction temperature of 330° C., and generates large amounts of reaction by-products.

In summary, in order to achieve economically acceptable reaction yield of caprolactam, most of the prior art processes were conducted at reaction temperatures of 270° C. or higher, and the reaction pressure typically exceeds 70 bar. Furthermore, in order to avoid the production of side-products (including polymers and/or oligmers), the reactant concentration in the feed was typically limited to less than 10 wt %. Catalysts were avoided in caprolactam manufacturing, mainly because of their tendency to cause undesired polymerization or oligmerization, which would lower the reaction yield and cause post-reaction separation problems. Furthermore, the high reaction temperature of the caprolactam manufacturing processes also tend to cause catalysts to be quickly deactivated, thus rendering a catalyzed process economically unattractive.

SUMMARY OF THE INVENTION

The primary object of the present invention is to develop an improved method for making caprolactam from aminohexanoic acid or aminohexanoate. More specifically, the primary object of the present invention is to develop an improved method for making caprolactam from aminohexanoic acid or aminohexanoate which can be conducted at a relatively low reaction temperature (between 140° and 300° C., preferably between 150° and 200° C.) and which can effectively utilize desirably high reactant concentrations (between 5 and 50 wt %, preferably between 5 and 30 wt %) in the reaction.

In the present invention, which counters the conventional wisdom of avoiding using catalyst, a catalyst is used in the preparation of caprolactam. The catalyst used in the present invention contains one or more metal oxides selected from the group consisting of zirconium oxide ($ZrO_2$), silicon dioxide ($SiO_2$), titanium dioxide ($TiO_2$), tin dioxide ($SnO_2$), barium oxide (BaO), calcium oxide (CaO), magnesium oxide (MgO), aluminum oxide ($A_2O_3$), zinc oxide (ZnO), and mixtures thereof. These catalysts can be prepared by first mixing salts (preferably nitrates or chlorides) of the above-mentioned metals with water or organic solvents. Then, 28% ammonia water or urea is added to the mixture. By controlling the solution pH between 8~11, metal hydroxides are precipitated. After filtration, rinsing with water, and oven drying, appropriately sized solids are obtained. These solids are calcined at 300°~1,000° C. to obtain the final catalyst products, which contain metal oxides. Other methods can be used for preparing the catalysts.

The catalysts disclosed in the present invention contain dual acid-base pairs of activity sites on the surface thereof; as a result, they exhibit the right acidity and/or basicity for the selective cyclodehydration of aminohexanoic acid or aminohexanoate esters involved in the present invention. Additionally, because the surface of the catalysts of the present invention does not contain active sites of relatively strong acidity, the problems of carbon deposition and polymerization can be eliminated. These advantageous properties allow a very high catalyst activity to be realized during caprolactam production while maximizing reaction yield and minimizing undesired side-product; they also prolong the life of the catalysts by avoiding catalyst poisoning.

In another embodiment of the present invention, small amounts of alkaline elements or alkaline earth elements are introduced during the preparation of the catalysts, to further improve the properties of the catalysts. To do this, the metal oxides prepared above are pickled in an aqueous solution containing minute mounts of alkaline or alkaline earth elements for several hours. After filtration, drying, and calcining at a temperature of 300°~1,000° C., a superior, extremely high activity dehydrating catalyst can be obtained.

The method disclosed in the present invention, which utilizes metal oxide catalysts containing acid-base pairs of activity sites, provides many superior advantages, including high reaction rate at relatively low reaction temperature, extremely high reactant conversion and reaction yield, flexibility to use relatively inexpensive solvents as reaction media, and minimum reaction waste. Another superior advantage of the method disclosed in the present invention is that it allows high reactant concentrations to be employed in the reaction, at least about twice as high as those of the prior art processes, without compromising conversion or reaction yield. Because of these advantageous features provided by the method disclosed in the present invention, the cost of making caprolactam is substantially reduced..

DETAILED DESCRIPTION OF THE PREFERRED EMBODIMENT

The present invention discloses an improved method for making caprolactam from aminohexanoic acid or aminohexanoate. The present invention counters the conventional wisdom of all the prior art processes by utilizing a novel approach which allows an appropriate catalyst to be used in the process of preparing caprolactam from aminohexanoic acid or aminohexanoate esters. The catalyst used in the present invention contains one or more metal oxides selected from the group consisting of zirconium oxide ($ZrO_2$), silicon dioxide ($SiO_2$), titanium dioxide ($TiO_2$), tin dioxide ($SnO_2$), barium oxide (BaO), calcium oxide (CaO), magnesium oxide (MgO), aluminum oxide ($A_2O_3$), Zinc oxide (ZnO), and mixtures thereof. These catalysts are prepared by first mixing salts (preferably nitrates or chlorides) of the above-mentioned metals with water or organic solvents. After adding 28% ammonia water or urea to the mixture and controlling the solution pH between 8~11, hydroxides are precipitated. After filtration, rinsing with water, and oven drying, appropriately sized solids are obtained. These solids are calcined at 300°~1,000° C. to obtain the metal oxides. To further improve the properties of the catalysts (i.e., further eliminating the problems of carbon accumulation and polymerization), the metal oxides are further subject to a pickling treatment, by which the metal oxides prepared above are pickled in an aqueous solution containing minute amounts of alkaline or alkaline earth elements for several hours. After filtration, drying, and calcining at 300°~1,000° C., a superior, extremely high activity dehydrating catalyst can be obtained.

The catalysts disclosed in the present invention have a surface containing acid-and-base-paired activity sites. As a result they exhibit the most appropriate acidity and/or basicity for the cyclodehydration of aminohexanoic acid or aminohexanoate esters involved in the present invention. The acid-base pairs of active sites on the surface of the catalysts of the present invention prevent the presence of active sites with excessively high acidity, thus the problems of carbon deposition and polymerization are eliminated. These advantageous properties allow a very high catalyst activity to be realized during caprolactam production, and prolong the life of the catalysts. Our test results showed that after the catalysts had been used for more than 1,000 hours, the yield of caprolactam was still better than 85 mol %. These results demonstrated the superior quality of the catalysts utilized in the present invention.

Another advantage of the method disclosed in the present invention is that it can use low-boiling-point solvents, such as methanol and ethanol, as the reaction solvent. Because aminohexanoate is soluble only in water, the presence of large amounts of water, according the classic LeChâtelier principle, would impede the dehydration reaction and lower the yield of caprolactam. Thus, as disclosed in German Patent DE-3,843,793 and U.S. Pat. No. 4,963,673, while water is used to dissolve the raw material aminohexanoate, large amounts, as high as 80 wt %, of o-xylene is added as the reaction solvent to form a two-phase reaction medium such that the reaction product caprolactam is dissolved in the o-xylene phase, while the reactant aminohexanoate remained dissolved in the aqueous phase. Such a two-phase reaction medium avoids the adverse effect of water which impedes the dehydration reaction. The high-boiling-point o-xylene (normal B.P.=144° C.) was selected as the second phase reaction medium because of the high reaction temperature (300° C.) and pressure (100 bar). In the process disclosed in the present invention, because the reaction is conducted at reaction temperatures of 200° C. or lower, a much greater flexibility of solvent selections can be accommodated. The present invention can use low-boiling-point solvents, such as methanol (B.P.=64.5° C.) or ethanol (B.P.=

78° C.), as reaction solvent. When either methanol or ethanol was used, the reaction yields were both greater than 85 mol %.

Comparing to all of the prior art processes for making caprolactam, the reaction process disclosed in the present invention is characterized in that it can be conducted in a much milder reaction condition, and because the catalyst active sites contain balanced acid-base pairs, no excessively high acidic active sites are present and the possibility of polymerization reactions is effectively thwarted.

In the process disclosed in the present invention, it is preferred that the cyclodehydration be conducted at a reaction temperature between 140° and 300° C., more preferably between 150° and 200° C. When the reaction temperature falls below 140° C., although the reaction will still proceed, a relatively lower reaction yield would be experienced, and the reaction rate is slowed. On the other hand, when the reaction temperature exceeds 280° C., a higher reaction pressure will be required and the extent of polymerized by-products will also increase. The reaction pressure is dictated by the reaction temperature. Typically a reaction pressure that can adequately maintain the reaction medium in liquid phase would suffice. No noticeable difference in the reaction yield of caprolactam was observed when the reaction pressure was varied between 20 and 60 atm. The weight-based hourly space velocity of the feed, measured as the weight of the feed per hour divided by the weight of the catalyst (referred to as "WHSV"), typically is maintained between 1 and 30 $hr^{-1}$, preferably between 3 and 20 $hr^{-1}$, if aminohexanoate is used as the raw material, and between 3 and 30 $hr^{-1}$, preferably between 5 and 30 $hr^{-1}$, if aminohexanoic acid is used as the raw material. The concentration of the aminohexanoic acid feed can be between 3 and 50 wt %, or preferably between 5 and 30 wt %.

With the novel cyclodehydration process disclosed in the present invention, not only the reaction yield of caprolactam can easily exceed 85 mol %, separation of the reaction product caprolactam from water and other reaction solvent (s) can also be easily effectuated. After the reaction, very-high purity crystalline caprolactam can be obtained with a simple reduced-pressure evaporation procedure.

In the examples that follow, the cyclodehydration reactions were conducted according to either one of the two main embodiments, one was conducted in a high-pressure batch reactor, and the other was conducted in a continuous fixed bed reactor. The former was conducted in a 300-ml high-pressure reactor, and the latter was in a stainless steel tube reactor ⅜" OD, 60 cm in length, and with a catalyst fix-bed height of 5~10 cm. The tube reactor has a pre-heating zone whose temperature was controlled using a heating tape to about 120° C.; on comparison, the temperature of the batch reactor was controlled using an electric heater to the desired temperature. The reaction feed aminohexanoic acid (or aminohexanoate) was charged into upper portion of the reactor using a metering pump. At the same time, nitrogen gas was introduced into the reactor at a rate of 30 ml/min, and the feed rate was maintained at 10 g/hr~100 g/hr. The pressure inside the reactor was regulated with a back pressure regulator to about 20~60 atm. After the completion of the reaction, the reaction product was condensed using a −5° C. circulating cooling pump and collected. The collected samples were titrated to determine their pH, and the concentration of caprolactam was measured using gas chromatography. In all the Examples, including the Comparative Examples, the conversion of aminohexanoic acid (or aminohexanoate) was determined by first measuring the acid amounts of the reaction solution before and after reaction using a KOH titrator, then was calculated using Formula (1) as follows:

Formula (1):

Conversion of aminohexanoic acid (or ester) (mol %) =

$$\frac{\text{acid amount before reaction} - \text{acid amount after reaction}}{\text{acid amount before reaction}} \times 100\%$$

In Formula (1), the acid amount is the acid amount of the aminohexanoic acid (or the equivalent of aminohexanoate ester).

The reaction yield of caprolactam is determined by measuring the concentration of caprolactam in the product solution, then calculated according to Formula (2) as follows:

Formula (2):

Reaction yield of caprolactam (mol %) =

$$\frac{\text{No. of moles of caprolactam in the reaction product}}{\text{No. of moles of aminohexanoic acid}} \times 100\%$$
(or ester) in the feed stream The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

Example 1

214 g of zirconium oxychloride ($ZrOCl_2 \cdot H_2O$) and 19 g of titanium tetrachloride ($TiCl_4$) were added to anhydrous ethanol and thoroughly mixed. Ammonia water was added to the solution, which then became viscositied (i.e., thickened). When the pH of the solution reached 10, the ammonia water was stopped. After filtration, washing with water, drying, calcining at 550° C. for 4 hours, pressing, and grinding to particle sizes of 30~50 mesh, a mixture of zirconium oxide and titanium oxide was obtained. These formed the catalyst composition to be used in this example. The zirconium oxide and titanium oxide so obtained both contained acid-base pairs of active sites.

10 g of catalysts prepared above were added into a 300-ml high-pressure vessel, then 200 ml of 15 wt % methyl aminohexanoate solution (in ethanol) were added. After purging with nitrogen, the reactor temperature was raised to 200° C. The reaction pressure was maintained at a pressure gauge reading of 22 atm. After three hours, the reactor was cooled to room temperature, and the reaction product was removed. One gram of the reaction product was titrated to measure its acid amount, and another gram of the reaction product was analyzed using GC to measure the caprolactam concentration. The results showed the conversion of methyl aminohexanoate was 100 mol %, and the reaction yield of caprolactam was 93.6 mol %.

Example 2

296 g of zirconium oxychloride ($ZrOCl_2 \cdot H_2O$) and 26 g of tin tetrachloride ($SnCl_4$) were added to ethylene glycol and thoroughly mixed. Ammonia water was added to the solution, which then became viscosified. When the pH of the solution reached 9, the ammonia water was stopped. After filtration, washing with water, drying, calcining at 700° C.

for 4 hours, pressing, and grinding to particle sizes of 30–50 mesh, a mixture of zirconium oxide and tin oxide was obtained. These formed the catalyst composition to be used in this example. As in the previous example, the zirconium oxide and tin oxide both contained acid-base pairs of active sites.

10 g of catalysts prepared above were added into a 300-ml high-pressure vessel, then 200 ml of 15 wt % octyl aminohexanoate solution (in ethanol) were added. After purging with nitrogen, the reactor temperature was raised to 250° C. The reaction pressure was maintained at a pressure gauge reading of 60 atm. After three hours, the reactor was cooled to room temperature, and the reaction product was removed. One gram of the reaction product was titrated to measure its acid amount, and another gram of the reaction product was analyzed using GC to measure the caprolactam concentration. The test results showed the conversion rate of octyl aminohexanoate was 93.8 mol %, and the reaction yield of caprolactam was 86.6 mol %.

Example 3

214 g of zirconium oxychloride ($ZrOCl_2.H_2O$) was dissolved to water and thoroughly mixed. Ammonia water was added to the solution, which cause the solution to become viscosified. When the pH of the solution reached 10, ammonia water was stopped. After filtration, washing with water, drying, calcining at 600° C. for 4 hours, pressing, and grinding to particle sizes of 30–50 mesh, zirconium oxide was obtained. This formed the catalyst composition to be used in this example. As in the previous examples, the zirconium oxide contained acid-base pairs of active sites.

10 g of zirconium oxide catalysts prepared above were added into a 300-ml high-pressure vessel, then 200 ml of 15 wt % aminohexanoic solution (in ethanol) were added. After purging with nitrogen, the reactor temperature was raised to 200° C. The reaction pressure was maintained at a pressure gauge reading of 22 atm. After three hours, the reactor was cooled to room temperature, and the reaction product was removed. One gram of the reaction product was titrated to measure its acid amount, and another gram of the reaction product was analyzed using GC to measure the caprolactam concentration. The test results showed the conversion of aminohexanoic acid was 100 mol %, and the reaction yield of caprolactam was 100 mol %.

Comparative Example 1

The reaction procedure was similar to the second part of Example 3, except that no zirconium oxide was added. Test results showed the conversion of aminohexanoic acid was 78.1 mol %, and the reaction yield of caprolactam was 70.0 mol %.

Examples 4 through 7

The procedures in Examples 4 through 7 were identical to that in Example 1, except that nitrates of barium, silicon, zinc, and magnesium, respectively, and zirconium oxynitrates, were used in preparing the catalyst composition, instead of the titanium chloride and zirconium oxychloride, respectively, used in Example 1. The catalyst compositions and reaction results of these examples are summarized in Table 1.

TABLE I

| Example | Catalyst Composition | Reaction Temperature (°C.) | Conversion (mol %) | Reaction Yield (mol %) |
|---|---|---|---|---|
| Example 4 | Ba—Zr | 250 | 100 | 95.6 |
| Example 5 | Si—Zr | 250 | 100 | 92.0 |
| Example 6 | Zn—Zr | 250 | 100 | 94.2 |
| Example 7 | Mg—Zr | 250 | 100 | 97.8 |

Results in Table 1 show that the conversion and reaction yield using barium oxide/zirconium oxide mixture (prepared from barium nitrate/zirconium oxynitrate) were 100 mol % and 95.6 mol %, respectively; the conversion and reaction yield using silicon oxide/zirconium oxide mixture (prepared from silicon nitrate/zirconium oxynitrate) were 100 mol % and 92.0 mol %, respectively; the conversion and reaction yield using zinc oxide/zirconium oxide mixture (prepared from zinc nitrate/zirconium oxynitrate) were 100 mol % and 94.2 mol %, respectively; and the conversion and reaction yield using magnesium oxide/zirconium oxide mixture (prepared from magnesium nitrate/zirconium oxynitrate) were 100 mol % and 97.8 mol %, respectively.

Examples 8 through 11

The procedures in Examples 8 through 11 were identical to those in Example 3, except that oxychlorides of titanium, aluminum, calcium, and tin were used, respectively, in preparing the catalyst composition, instead of the zirconium chloride used in Example 3. The catalyst compositions and reaction results of these examples are summarized in Table 2.

TABLE II

| Example | Catalyst Composition | Reaction Temperature (°C.) | Conversion (mol %) | Reaction Yield (mol %) |
|---|---|---|---|---|
| Example 8 | $TiO_2$ | 200 | 99.2 | 95.0 |
| Example 9 | $Al_2O_3$ | 200 | 90.3 | 87.9 |
| Example 10 | CaO | 200 | 100.0 | 88.1 |
| Example 11 | $SnO_2$ | 200 | 95.7 | 92.4 |

Results in Table 2 show that the conversion and reaction yield using titanium oxide (prepared from titanium oxychloride) were 99.2 mol % and 95.0 mol %, respectively; the conversion and reaction yield using aluminum oxide (prepared from aluminum oxychloride) were 90.3 mol % and 87.9 mol %, respectively; the conversion and reaction yield using calcium oxide (prepared from calcium oxychloride) were 100 mol % and 88.1 mol %, respectively; and the conversion and reaction yield using tin oxide (prepared from tin oxychloride) were 95.7 mol % and 92.4 mol %, respectively.

Example 12

The procedure in Example 12 was identical to that in Example 3, except that concentration of the aminohexanoic acid was 30 wt %. Results show that the conversion and reaction yield in Example 12 were 92.3 mol % and 83.7 mol %, respectively.

Comparative Example 2

The procedure in Comparative Example 2 was identical to that in Example 12, except that no zirconium oxide catalyst was added. Results show that the conversion and reaction yield in Comparative Example were 18.7 mol % and 17.4 mol %, respectively.

Example 13

The procedure in Example 13 was identical to that in Example 3, except that n-butyl alcohol was used as the reaction solvent (instead of ethanol). Results show that the conversion and reaction yield in Example 13 were 94.8 mol % and 94.8 mol %, respectively.

Example 14

The procedure in Example 14 was identical to that in Example 3, except that o-xylene was used as the reaction solvent (instead of ethanol). Results show that the conversion and reaction yield in Example 14 were 99.1 mol % and 82.8 mol %, respectively.

Example 15

3 g of the zirconium oxide obtained in Example 3 was filled into a ⅜"-OD stainless steel tube reactor, which had a length of 60 cm. A pre-heating zone was provided prior to the tube reactor which was heated with heating tape to maintain a temperature of 120° C., while the temperature of the reactor itself was maintained at 180° C. with an electric heater. Reaction feed, which contained 15 wt % of aminohexanoic acid in ethanol was delivered, using a metering pump, into pre-heating zone, where the reactant stream was mixed with nitrogen (at a rate of 30 ml/min) before both entered the tube reactor. The feed rate of aminohexanoic acid was 20 g/hr, representing a WHSV of 6.7 $hr^{-1}$. The pressure inside the tube reactor was maintained, using a back-pressure regulated, at 30 atm. The reaction product was cooled by a $-5°$ C. condenser, and collected with a sample collector. One gram of the reaction product after obtained 3~3.5 hours of operation was titrated to measure it acid amount, which was converted into conversion (of aminohexanoic acid). Another gram of the same reaction product was analyzed using GC to measure the caprolactam concentration, so as to calculate the reaction yield. Results show that the conversion and reaction yield in Example 15 were 96.6 mol % and 87.5 mol %, respectively.

Example 16

The procedure in Example 16 was identical to that in Example 15 (using zirconium oxide as the catalyst), except that the reaction temperature was maintained at 140° C. Results show that the conversion and reaction yield in Example 16 were 86.0 mol % and 76.6 mol %, respectively.

Comparative Example 3

The procedure in Comparative Example 3 was identical to that in Example 15, except that the tube reactor was filled with inert ceramic particles (instead of zirconium oxide), and that the reaction temperature was maintained at 250° C. Results show that the conversion and reaction yield in Comparative Example 3 were 70.0 mol % and 33.4 mol %, respectively.

Example 17

The procedure in Example 17 was identical to that in Example 15, except that the concentration of aminohexanoic acid in the feed stream was 30 wt %, instead of 15 wt %. Results show that the conversion and reaction yield in Example 17 were 92.2 mol % and 85.8 mol %, respectively.

Comparative Example 4

The procedure in Comparative Example 4 was identical to that in Example 17, except that the tube reactor was filled with inert ceramic particles (instead of zirconium oxide), and that the reaction temperature was maintained at 200° C. Results show that the conversion and reaction yield in Comparative Example 4 were 22.4 mol % and 15.2 mol %, respectively.

Examples 18 through 21

The procedures in Examples 18 through 21 were identical to that in Example 15, except that the reaction temperatures and the weight-based hour space velocity, WHSV, were different. These variables and the reaction results of these examples are summarized in Table 3.

TABLE 3

| Example | WHSV ($hr^{-1}$) | Reaction Temperature (°C.) | Conversion (mol %) | Reaction Yield (mol %) |
|---|---|---|---|---|
| Example 18 | 3.3 | 160 | 97.8 | 86.8 |
| Example 19 | 10.0 | 200 | 98.0 | 86.5 |
| Example 20 | 16.7 | 220 | 95.7 | 90.1 |
| Example 21 | 26.7 | 240 | 99.8 | 85.8 |

Results in Table 3 show that the conversion and reaction yield at WHSV of 3.3 $hr^{-1}$ and reaction temperature of 160° C. were 97.8 mol % and 86.8 mol %, respectively; the conversion and reaction yield at WHSV of 10.0 $hr^{-1}$ and reaction temperature of 200° C. were 98.0 mol % and 86.5 mol %, respectively; the conversion and reaction yield at WHSV of 16.7 $hr^{-1}$ and reaction temperature of 220° C. were 95.7 mol % and 90.1 mol %, respectively; the conversion and reaction yield at WHSV of 26.7 $hr^{-1}$ and reaction temperature of 240° C. were 99.8 mol % and 85.8 mol %, respectively.

Examples 22 through 24

The procedures in Examples 22 through 24 were identical to that in Example 15, except that the reaction pressure was different. These variables and reaction results of these examples are summarized in Table 4.

TABLE 4

| Example | Reaction Pressure (atm) | Reaction Temperature (°C.) | Conversion (mol %) | Reaction Yield (mol %) |
|---|---|---|---|---|
| Example 22 | 20 | 180 | 97.1 | 86.1 |
| Example 23 | 40 | 180 | 95.7 | 86.3 |
| Example 24 | 60 | 180 | 97.7 | 86.3 |

Results in Table 4 show that the conversion and reaction yield at reaction pressure of 20 atm and reaction temperature of 180° C. were 97.1 mol % and 86.1 mol %, respectively; the conversion and reaction yield at reaction pressure of 40 atm and reaction temperature of 180° C. were 95.7 mol % and 86.3 mol %, respectively; the conversion and reaction yield at reaction pressure of 60 atm and reaction temperature of 180° C. were 97.7 mol % and 86.3 mol %, respectively.

Example 25

The procedure in Example 25 was identical to that in Example 15, but was continued for more than 1,000 hours to observe the active catalyst life. Results show that the process disclosed in the present invention not only provides excellent conversion and reaction yield, it also allow the catalyst to maintain a long active life. Table 5 shows the conversion and reaction yields at various stages of the operation.

| Operation Time (hr) | 20 | 101 | 238 | 318 | 405 | 501 | 628 | 718 | 1,069 |
|---|---|---|---|---|---|---|---|---|---|
| Conversion (mol %) | 100.0 | 100.0 | 100.0 | 100.0 | 100.0 | 100.0 | 99.3 | 99.7 | 98.8 |
| Reaction Yield (mol %) | 91.1 | 89.2 | 93.6 | 87.9 | 89.9 | 87.7 | 87.9 | 91.7 | 89.6 |

Table 5 shows that, even after more 1,000 hours of operation, excellent conversion of aminohexanoic acid (98.8 mol %) and reaction yield (89.6 mol %) were still observed.

The above results indicate that superior results, as indicated by the excellent conversions of the reactant, which can be either aminohexanoic acid or aminohexanoate ester, and the excellent yields of caprolactam, were observed from the process disclosed in the present invention. Furthermore, the process disclosed in the present invention can be advantageously conducted at relatively low reaction temperature and pressure, and the catalysts exhibited excellent catalyst life.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method of making caprolactam from aminohexanoic acid or aminohexanoate ester comprising the steps of:
   (a) obtaining a reactor containing at least one catalyst, said catalyst being a metal oxide having acid-base-paired active sites;
   (b) charging a reaction feed into said reactor, said reaction feed containing a reactant, which is either amniohexanoic acid or $C_1$ to $C_{12}$ alkyl aminohexanoate ester, and a solvent;
   (c) reacting said reaction feed at a reaction temperature between 140° and 300° C. and a reaction pressure between 10 and 100 atm, to form a product stream; and
   (d) separating caprolactam from the product stream;
   wherein said metal oxide catalyst is prepared by a process which comprises the following steps:
   (e) dissolving at least a metal salt, which is not a metal oxide, in a second solvent to form a metal salt solution, wherein:
      (i) said metal salt contains a metal element selected from the group consisting of silicon, titanium, tin, barium, calcium, magnesium, aluminum, and zinc;
      (ii) said second solvent is selected from the group consisting of water, alcohol, ether, and mixtures thereof; and
      (iii) said metal salt is a salt which is soluble in said second solvent;
   (f) adjusting the pH of said metal salt solution to be between 8 and 11, to thereby cause a formation and precipitation of a metal hydroxide; and
   (g) calcining said metal hydroxide at 300° to 1,000° C. to form a metal oxide.

2. The method of making caprolactam from aminohexanoic acid or aminohexanoate ester according to claim 1 wherein said metal oxide is selected from the group consisting of zirconium oxide ($ZrO_2$), silicon dioxide ($SiO_2$), titanium dioxide ($TiO_2$), tin dioxide ($SnO_2$), barium oxide (BaO), calcium oxide (CaO), magnesium oxide (MgO), aluminum oxide ($Al_2O_3$), zinc oxide (ZnO), and mixtures thereof.

3. The method of making caprolactam from aminohexanoic acid or aminohexanoate ester according to claim 1 wherein said reactor is a fixed bed reaction and said reaction feed is continuously charged into said reactor at a weight-based space velocity between 1 and 30 $hr^{-1}$ and a reactant concentration between 3 and 50 wt %.

4. The method of making caprolactam from aminohexanoic acid or aminohexanoate ester according to claim 3 wherein said reactor feed contains a reactant concentration between 15 and 30 wt %.

5. The method of making caprolactam from aminohexanoic acid or aminohexanoate ester according to claim 1 wherein said solvent is selected from the group consisting of water, $C_1$ to $C_4$ alcohol, benzene, toulene, xylene, and mixtures thereof.

6. The method of making caprolactam from aminohexanoic acid or aminohexanoate ester according to claim 1 wherein said solvent is selected from the group consisting of water, $C_1$ to $C_4$ alcohol, and mixtures thereof.

7. The method of making caprolactam from aminohexanoic acid or aminohexanoate ester according to claim 1 wherein said metal salt is metal chloride.

8. The method of making caprolactam from aminohexanoic acid or aminohexanoate ester according to claim 1 wherein said metal salt is metal nitrate.

9. The method of making caprolactam from aminohexanoic acid or aminohexanoate ester according to claim 1 wherein said second solvent is selected from the group consisting of ethanol, ethylene glycol, and mixtures thereof.

10. The method of making caprolactam from aminohexanoic acid or aminohexanoate ester according to claim 1 wherein said process for preparing said metal oxide catalyst further comprises the steps of:
   (d) soaking said metal oxide after step (c) in an aqueous solution containing alkaline or alkaline earth metal ions; and
   (e) calcining said metal oxide that has been soaked with alkaline or alkaline earth metal ions in step (d) at a temperature between 300° and 1,000° C.

11. The method of making caprolactam from aminohexanoic acid or aminohexanoate ester according to claim 1 wherein said catalyst is zirconium oxide and said reaction temperature in step (c) is about 180° C.

12. The method of making caprolactam from aminohexanoic acid or aminohexanoate ester according to claim 1 wherein said catalyst is zirconium oxide and said reaction temperature in step (c) is about 180° C., and said feed contains 30 wt % of amniohexanoic acid or $C_1$ to $C_{12}$ alkyl aminohexanoate ester.

* * * * *